(12) United States Patent
Liu

(10) Patent No.: US 10,980,768 B2
(45) Date of Patent: Apr. 20, 2021

(54) COMPOSITION CONTAINING CARBOPLATIN AND USE

(71) Applicant: SYN-NAT PRODUCTS ENTERPRISE LLC, Edison, NJ (US)

(72) Inventor: Xiaozhong Liu, Potomac, MD (US)

(73) Assignee: SYN-NAT PRODUCTS ENTERPRISE LLC, Potomac, MD (US)

(*) Notice: Subject to any disclaimer, the term of this patent is extended or adjusted under 35 U.S.C. 154(b) by 7 days.

(21) Appl. No.: 15/736,170

(22) PCT Filed: Jun. 20, 2016

(86) PCT No.: PCT/US2016/038333
§ 371 (c)(1),
(2) Date: Dec. 13, 2017

(87) PCT Pub. No.: WO2016/205782
PCT Pub. Date: Dec. 22, 2016

(65) Prior Publication Data
US 2018/0169055 A1    Jun. 21, 2018

Related U.S. Application Data

(60) Provisional application No. 62/182,124, filed on Jun. 19, 2015.

(51) Int. Cl.

| | | |
|---|---|---|
| *A61K 31/282* | (2006.01) | |
| *A61K 31/198* | (2006.01) | |
| *A61K 31/12* | (2006.01) | |
| *A61K 31/519* | (2006.01) | |
| *A61K 31/69* | (2006.01) | |
| *A61K 31/513* | (2006.01) | |
| *A61K 36/886* | (2006.01) | |
| *A61P 35/02* | (2006.01) | |
| *A61P 13/12* | (2006.01) | |
| *A61P 35/00* | (2006.01) | |
| *A61K 9/00* | (2006.01) | |

(52) U.S. Cl.
CPC .......... *A61K 31/282* (2013.01); *A61K 9/0053* (2013.01); *A61K 31/12* (2013.01); *A61K 31/198* (2013.01); *A61K 31/513* (2013.01); *A61K 31/519* (2013.01); *A61K 31/69* (2013.01); *A61K 36/886* (2013.01); *A61P 13/12* (2018.01); *A61P 35/00* (2018.01); *A61P 35/02* (2018.01)

(58) Field of Classification Search
CPC .... A61K 31/282; A61K 9/0053; A61K 31/12; A61K 31/198; A61K 31/513; A61K 31/519; A61K 31/69; A61K 36/886; A61P 35/02; A61P 13/12

USPC ........................................................ 514/492
See application file for complete search history.

(56) References Cited

U.S. PATENT DOCUMENTS

| | | |
|---|---|---|
| 5,922,689 A | 7/1999 | Shaw |
| 6,297,245 B1 | 10/2001 | Shaw |
| 6,340,770 B1 | 1/2002 | Kwon et al. |
| 6,699,901 B1 * | 3/2004 | Yang ........................ A61P 35/00 514/492 |
| 7,927,613 B2 | 4/2011 | Almarsson et al. |
| 8,247,445 B2 | 8/2012 | Kay et al. |
| 9,447,130 B1 | 9/2016 | Liu et al. |
| 2003/0103896 A1 | 6/2003 | Smith |
| 2004/0152766 A1 | 8/2004 | Au-Yeung et al. |
| 2005/0165093 A1 | 7/2005 | Wang et al. |
| 2007/0197517 A1 | 8/2007 | Jani et al. |
| 2008/0063642 A1 | 3/2008 | Adelman et al. |
| 2008/0161251 A1 | 7/2008 | Curry et al. |
| 2009/0281319 A1 | 11/2009 | Du Preez |
| 2010/0068178 A1 | 3/2010 | Gokaraju et al. |
| 2011/0287110 A1 * | 11/2011 | Dewhirst ................ A61K 31/27 424/649 |
| 2018/0085377 A1 | 3/2018 | Liu |
| 2018/0179240 A1 | 6/2018 | Liu |
| 2018/0186822 A1 | 7/2018 | Liu |
| 2018/0289662 A1 | 10/2018 | Liu |

FOREIGN PATENT DOCUMENTS

| | | | |
|---|---|---|---|
| CN | 103494838 A | | 1/2014 |
| CN | 104127402 A | * | 11/2014 |
| CN | 104127402 A | | 11/2014 |
| CN | 104693245 A | | 6/2015 |
| EP | 1186610 A1 | | 3/2002 |
| WO | WO 2011/029415 A1 | | 3/2011 |
| WO | WO 2015/058067 A1 | | 4/2015 |
| WO | WO 2016/172393 A1 | | 10/2016 |
| WO | WO 2016/187191 A1 | | 11/2016 |
| WO | WO 2016/205782 A1 | | 12/2016 |

(Continued)

OTHER PUBLICATIONS

Extended European Search Report dated Mar. 11, 2019 in European Patent Application No. 16812606.8, 10 pages.

(Continued)

*Primary Examiner* — Yevgeny Valenrod
(74) *Attorney, Agent, or Firm* — Nixon & Vanderhye, PC

(57) ABSTRACT

This invention discloses pharmaceutical use of a dicycloplatin (DCP) for the prophylaxis or treatment of leukemia, renal adenocarcinoma or melanoma. Methods using DCP, either alone or in combination with at least one additional therapeutic agent or adjuvant therapy agent, are also disclosed.

11 Claims, 6 Drawing Sheets

(56) References Cited

FOREIGN PATENT DOCUMENTS

| WO | WO 2016/205785 A1 | 12/2016 |
|---|---|---|
| WO | WO 2016/210418 A1 | 12/2016 |

OTHER PUBLICATIONS

Yu, J. J., et al., "Dicycloplatin, a Novel Platinum Analog in Chemotheraphy: Synthesis of Chinese Pre-clinical and Clinical Profile and Emerging Mechanistic Studies," Anticancer Res., 34:455-464 (2014).

Li, GQ et al., "Effect of Dicyclopatin, a Novel Platinum Chemotherapeutical Drug, on Inhibiting Cell Growth and Inducing Cell Apoptosis," PLOS One, 7(11):e48394 (2012).

Omar, E.K. et al., "Does the Key to Treat Rheumatoid Nodules Lie with Oncology?—Is Cisplatin an Option?," BioMed Central Musculoskeletal Disorders, 14 (Suppl. 1): A5, BioMed Central (2013).

Kreiner, B. et al., "Neuroendocrine Carcinoma of the Seminal Vesicles Presenting with Lambert Eaton Syndrome: a Case Report," Journal of Medical Case Reports, 4:320, p. 1-4, BioMed Central (2010).

Li, S. et al., "Phase I Clinical Trial of the Novel Platin Complex Dicycloplatin: Clinical and Pharmacokinetic Results," Int'l Journal of Clinical Pharmacology and Therapeutics, vol. 51, No. 2, pp. 96-105 (2013).

Liu, KJ et al., "A Double-Blind, Randomized Phase II Study of Dicycloplatin Plus Paclitaxel Versus Carboplatin Plus Paclitaxel as First-Line Therapy for Patients with Advanced Non-Small-Cell Lung Cancers," Arch Med Sci, 10, 4: 717-724, Elsevier, Netherlands (2014).

Yang, X. et al., "Determination Methods for the Anticancer Drug Dicycloplatin, a Supramolecule Assembled Through Hydrogen Bonding", Analyst, 140:2704-2712, The Royal Society of Chemistry (2015).

International Search Report of PCT/US2016/028720 dated Jul. 15, 2016, issued by the International Bureau.

International Search Report of PCT/US2016/032856 dated Aug. 16, 2016, issued by the International Bureau.

International Search Report of PCT/US2016/038340 dated Sep. 13, 2016, issued by the International Bureau.

International Search Report of PCT/US2016/039572 dated Sep. 23, 2016, issued by the International Bureau.

International Search Report of PCT/US2016/038333 dated Sep. 28, 2016, issued by the International Bureau.

* cited by examiner

COMPOSITION CONTAINING CARBOPLATIN AND USE

FIELD OF THE INVENTION

The present invention relates to dicycloplatin (DCP) for the treatment of leukemia, renal adenocarcinoma or melanoma. Methods using the DCP, either alone or in combination with at least one additional therapeutic agent or adjuvant therapy agent, are disclosed.

BACKGROUND OF THE INVENTION

Leukemia, renal adenocarcinoma and melanoma are malignant cancers that claim hundreds of thousands of lives around the world every year. Researchers have been constantly pursuing new, safe and effective drugs and treatments.

Leukemia is a group of cancers that usually start in blood-forming tissues, such as the bone marrow, and cause a large number of abnormal blood cells to be produced and enter the bloodstream. The major types of leukemia at least include: acute or chronic myelogeneous leukemia, which involves the myeloid elements of bone marrow (white cells, red cells, megakaryocytes), and acute lymphoblastic leukemia (ALL) and chronic lymphocyclic leukemia (CLL), which involve the cells of the lymphoid lineage. More than 50 commercial drugs have been approved by the Food and Drug Administration (FDA) for different types of leukemia. In addition to single drug treatments, the combination of multiple drugs has been widely used. However, leukemia is very complex, and the selection of drugs depends on the types of leukemia. Additional drugs and treatments are still highly desirable.

Around 208,500 new cases of renal adenocarcinoma are diagnosed in the world each year, accounting for just under 2% of all cancers. The highest rates are recorded in Northern America and the lowest rates in Asian and African regions. Two most common types of renal adenocarcinoma are renal cell carcinoma (RCC) and transitional cell carcinoma (TCC) of the renal pelvis. Treatment for renal adenocarcinoma depends on the type and stage of the disease. Surgery is typically the mainstay of treatment and in many cases it does not involve chemotherapy and radiotherapy, as renal adenocarcinomas often do not respond to these treatments. The overall five year survival rates in the United States are 73%. New treatment methods are still required to further improve the survival rate.

Melanoma is a type of skin cancer which forms the pigment-containing cells known as melanocytes. Melanoma is highly dangerous if not diagnosed in the early stages and it causes the majority (75%) of deaths related to skin cancer. Globally, in 2012, melanoma occurred in 232,000 people and resulted in 55,000 deaths. Australia and New Zealand have the highest rates of melanoma in the world. It has become more common in the last 20 years in areas that are mostly Caucasian. The treatments of melanoma usually include surgical tumor removal.

The likelihood that the melanoma would come back or spread depends on how deeply tumor has penetrated the layers of the skin. Other treatments of melanomas, especially melanomas that come back spread, include chemotherapy, immunotherapy, and radiation therapy. Five year survival rates in the United States are on average 91%. Depending on various parameters (tumor thickness, body location, age, etc.), the removal of nearby lymph nodes in a melanoma patient may be recommended for treatment. For advanced stages of the disease, such as when the melanoma has spread to other parts of the body, treatments like immunotherapy or chemotherapy are usually recommended. Many of these treatments are still experimental and their use may be limited. Overall, more effective treatments of melanoma are still highly desirable.

Dicycloplatin (DCP) is a super molecule composed of carboplatin (CBP) and 1,1-cycyclobutane dicarboxylate (CBDCA) joined by strong hydrogen bonds. Preclinical studies have shown that DCP overcomes the problem of CBP instability in aqueous solution and maintains its anti-cancer effects. Clinical evaluation in a Phase I dose-escalation study in patients showed that DCP was tolerated at doses ranging from 100 to 550 $mg/m^2$ and had potential efficacy in cancer patients. DCP showed favorable bioavailability and stability in vivo, and the recommended dosage for DCP-containing chemotherapy is 450 $mg/m^2$. DCP is currently being investigated as a monotherapy in prostatic carcinoma and in combination with paclitaxel in a non-lung cancer study. Chemical structure of DCP is shown as formula I:

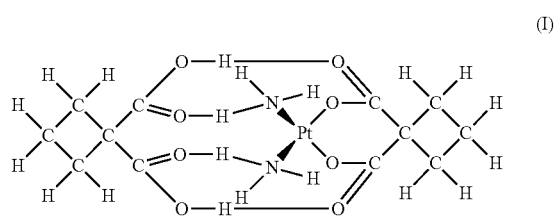

(I)

Although some studies demonstrated certain anti-tumor effects of DCP, the specific effects on particular cancers are not clearly illustrated. Due to the complexity and distinct nature of different types of cancer, the effects of DCP still need to be further explored. The current invention demonstrates DCP efficacy in the prophylaxis or treatment of leukemia, renal adenocarcinoma and melanoma.

SUMMARY OF THE INVENTION

The present invention relates to the pharmaceutical use of dicycloplatin (DCP) in the prophylaxis or treatment of leukemia, renal adenocarcinoma or melanoma. In one aspect, the present invention relates to a method of killing malignant cancer cells by contacting a cancer cell with DCP, wherein the cancer is leukemia, renal adenocarcinoma or melanoma. In addition, the present invention relates to a method of treating or preventing a disease in a subject, comprising administering a pharmaceutical composition comprising DCP to the subject, wherein the disease is leukemia, renal adenocarcinoma or melanoma. In some embodiments, the pharmaceutical composition consists of DCP; in other embodiments, the pharmaceutical composition comprises DCP. In some embodiments, the pharmaceutical composition comprises an effective amount of DCP and at least one additional therapeutic agent or adjuvant therapy agent.

In one aspect, the present invention relates to the use of DCP in the prophylaxis or treatment of leukemia. In some embodiments, the invention relates to a method of treating or preventing leukemia in a subject, comprising administering a pharmaceutical composition comprising an effective amount of DCP to the subject. In some embodiments, the invention relates to a method of killing a malignant cell in a subject suffering from leukemia, comprising administering a pharmaceutical composition comprising an effective amount of DCP to the subject.

In another aspect, the present invention relates to the use of DCP in the prophylaxis or treatment of renal adenocarcinoma. In some embodiments, the invention relates to a method of treating or preventing renal adenocarcinoma in a subject, comprising administering a pharmaceutical composition comprising an effective amount of DCP to the subject. In some embodiments, the invention relates to a method of killing a malignant cell in a subject suffering from renal adenocarcinoma, comprising administering a pharmaceutical composition comprising an effective amount of DCP to the subject.

In one aspect, the present invention relates to the use of DCP in the prophylaxis or treatment of melanoma. In some embodiments, the invention relates to a method of treating or preventing melanoma in a subject, comprising administering a pharmaceutical composition comprising an effective amount of DCP to the subject. In some embodiments, the invention relates to a method of killing a malignant melanocyte in a subject suffering from melanoma, comprising administering a pharmaceutical composition comprising an effective amount of DCP to the subject.

DETAILED DESCRIPTION OF THE INVENTION

Figure 1:
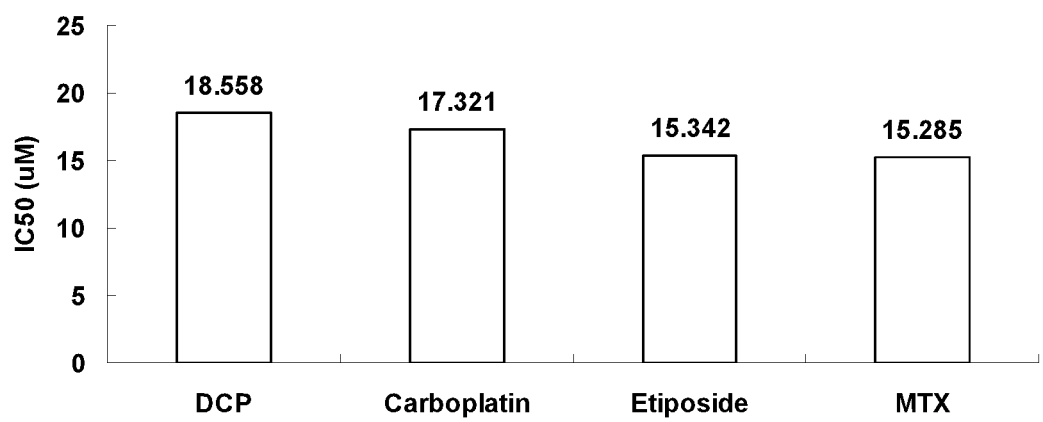
FIG. 1 shows the $IC_{50}$ values of tested and control agents in HL-60 cells, a cell line derived from an acute promyelocytic leukemia patient.

Unless defined otherwise, all technical and scientific terms used herein have the same meaning as is commonly understood by one of skill in the art to which this invention belongs. All patents and publications referred to herein are incorporated by reference in their entireties.

The term "effective amount" or "therapeutically effective amount" refers to that amount of a compound or combination of compounds as described herein that is sufficient to effect the intended application including, but not limited to, prophylaxis or treatment of diseases.

A therapeutically effective amount may vary depending upon the intended application (in vitro or in vivo), or the subject and disease condition being treated (e.g., the weight, age and gender of the subject), the severity of the disease condition, the manner of administration, etc. which can readily be determined by one of ordinary skill in the art. The term also applies to a dose that will induce a particular response in target cells and/or tissues (e.g., the reduction of cell proliferation and/or morphological alteration of the tissue). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A "prophylactic effect" (e.g. terms such as "prophylaxis," "prevent" and "reducing the likelihood for developing") includes delaying or eliminating the appearance of a disease or condition, delaying or eliminating the onset of symptoms of a disease or condition, slowing, halting, or reversing the progression of a disease or condition, or any combination thereof by administering a drug before the onset of the disease or condition. A "treatment effect" (e.g. with terms such as "treatment" and "treat") includes reducing or eliminating the appearance of a disease or condition, reducing or eliminating the symptoms of a disease or condition, slowing, halting, or reversing the progression of a disease or condition, or any combination thereof by administering a drug after the onset of the disease or condition.

A "subject" as the term is used herein, refers to a human or non-human animal. In some embodiments, the subject is a mammal. In some embodiments, the subject is human.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, or from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

Compounds used in the present invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

The present invention in various aspects and embodiments involves uses of DCP for the prophylaxis or treatment of leukemia, renal adenocarcinoma or melanoma and methods of treating or preventing leukemia, renal adenocarcinoma or melanoma by administering a pharmaceutical composition comprising DCP.

In some embodiments, the administration of DCP treats or prevents the diseases by modulating the immunological response of the subject. Particularly in some embodiments, DCP enhances the immunological response and in other embodiments, DCP reduces the immunological response. For example, in some embodiments DCP enhances or reduces the number and/or effectiveness of T cells; in some embodiments DCP enhances or reduces the number and/or effectiveness of B cells. The capability to modulate the immunological response may affect the efficacy of DCP in treating and/or preventing the proliferative diseases, immunological diseases, degenerative diseases, and other diseases.

In some embodiments, the active ingredient of the pharmaceutical composition may consist of DCP. In some embodiments, the pharmaceutical composition may comprise DCP and at least one additional therapeutic agent or adjuvant therapy agent. The additional therapeutic agent or adjuvant therapy agent may be selected from but is not limited to: folic acid, coenzyme Q10, curcumin, glutathione (GSH), aloe vera, oryzanol, 5-fluorouracil, bortezomib, or a combination thereof. Depending on the particular disease to be treated, the additional therapeutic agent or adjuvant therapy agent may include drugs already known. In some embodiments, the additional therapeutic agent or adjuvant therapy agent may include drugs that have already been clinically accepted to treat or prevent the disease.

In some embodiments, the pharmaceutical composition may comprise DCP and a pharmaceutically acceptable carrier or excipient. "Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

In some embodiments, the present invention provides a method of treating, preventing, reducing or alleviating the symptoms of, and/or slowing or halting the progress of leukemia in a subject in need thereof, the method comprising administrating to the subject an effective amount of a pharmaceutical composition comprising DCP. In some embodiments, the leukemia is acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, or T-cell leukemia caused by human T-lymphotropic virus (HTLV).

In some embodiments, the present invention provides a method of killing a malignant cell in a subject suffering from leukemia, comprising administering a pharmaceutical composition comprising an effective amount of DCP to the subject. In some embodiments, the malignant cell is a cancerous white blood cell and the subject is suffering from promyelocytic leukemia. In other embodiments, the malignant cell is a cancerous myeloblast and the subject is suffering from myelogenous leukemia.

In some embodiments, the active ingredient of the pharmaceutical composition consists of DCP. In some embodiments, the pharmaceutical composition further comprises at least one additional therapeutic agent or adjuvant therapy agent. In a specific embodiment, the additional therapeutic agent or adjuvant therapy agent may be selected from: folic acid, coenzyme Q10, curcumin, glutathione (GSH), aloe vera, oryzanol, 5-fluorouracil, and bortezomib. In some embodiments, the pharmaceutical composition comprises DCP and a pharmaceutically acceptable carrier or excipient.

In some embodiments, for prophylaxis or treatment of leukemia, the amount of DCP in the pharmaceutical composition administered to a subject may be about 0.005 to 20 mg/kg body weight, about 0.005 to 10 mg/kg body weight, about 0.005 to 5 mg/kg body weight, about 0.005 to 2.5 mg/kg body weight, 0.01 to 20 mg/kg body weight, about 0.01 to 10 mg/kg body weight, about 0.01 to 5 mg/kg body weight, about 0.01 to 2.5 mg/kg body weight, 0.1 to 20 mg/kg body weight, about 0.1 to 10 mg/kg body weight, about 0.1 to 5 mg/kg body weight, about 0.1 to 2.5 mg/kg body weight, 1 to 20 mg/kg body weight, about 1 to 10 mg/kg body weight, about 1 to 5 mg/kg body weight, or about 1 to 2.5 mg/kg body weight. In some embodiments, the amount of DCP is about 0.01 to 5 mg/kg body weight. In another embodiment, the amount of DCP is about 1 to 10 mg/kg body weight.

In some embodiments, for prophylaxis or treatment of leukemia, the pharmaceutical composition comprising the DCP is administered with injections or via the oral route. In some embodiments, for prophylaxis or treatment of leukemia, the pharmaceutical composition comprising the DCP is administered for at least one, two or three weeks.

In some embodiments, the present invention provides a method of treating, preventing, reducing or alleviating the symptoms of, and/or slowing or halting the progress of renal adenocarcinoma in a subject in need thereof, the method comprising administrating to the subject an effective amount of a pharmaceutical composition comprising DCP. In some embodiments, the renal adenocarcinoma is renal cell carcinoma, renal pelvis carcinoma, squamous cell carcinoma, juxtaglomerular cell tumor (reninoma), angiomyolipoma, Bellini duct carcinoma, clear-cell sarcoma of the kidney, mesoblastic nephroma, Wilms' tumor, or mixed epithelial stromal tumor.

In some embodiments, the present invention provides a method of killing a malignant renal cell in a subject suffering from renal adenocarcinoma, comprising administering a pharmaceutical composition comprising an effective amount of DCP to the subject. In some embodiments, the malignant renal cell is a renal carcinoma cell.

In some embodiments, the active ingredient of the pharmaceutical composition consists of DCP. In some embodiments, the pharmaceutical composition further comprises at least one additional therapeutic agent or adjuvant therapy agent. In a specific embodiment, the additional therapeutic agent or adjuvant therapy agent may be selected from: folic acid, coenzyme Q10, curcumin, glutathione (GSH), aloe vera, oryzanol, 5-fluorouracil, and bortezomib. In some embodiments, the pharmaceutical composition comprises DCP and a pharmaceutically acceptable carrier or excipient.

In some embodiments, for prophylaxis or treatment of renal adenocarcinoma, the amount of DCP in the pharmaceutical composition administered to a subject may be about 0.005 to 20 mg/kg body weight, about 0.005 to 10 mg/kg body weight, about 0.005 to 5 mg/kg body weight, about 0.005 to 2.5 mg/kg body weight, 0.01 to 20 mg/kg body weight, about 0.01 to 10 mg/kg body weight, about 0.01 to 5 mg/kg body weight, about 0.01 to 2.5 mg/kg body weight, 0.1 to 20 mg/kg body weight, about 0.1 to 10 mg/kg body weight, about 0.1 to 5 mg/kg body weight, about 0.1 to 2.5 mg/kg body weight, 1 to 20 mg/kg body weight, about 1 to 10 mg/kg body weight, about 1 to 5 mg/kg body weight, or about 1 to 2.5 mg/kg body weight. In some embodiments, the amount of DCP is about 0.01 to 5 mg/kg body weight. In another embodiment, the amount of DCP is about 1 to 10 mg/kg body weight.

In some embodiments, for prophylaxis or treatment of renal adenocarcinoma, the pharmaceutical composition comprising the DCP is administered with injections or via the oral route. In some embodiments, for prophylaxis or treatment of renal adenocarcinoma, the pharmaceutical composition comprising the DCP is administered for at least one, two or three weeks.

In some embodiments, the present invention provides a method of treating, preventing, reducing or alleviating the symptoms of, and/or slowing or halting the progress of melanoma in a subject in need thereof, the method comprising administrating to the subject an effective amount of a pharmaceutical composition comprising DCP. In some embodiments, the melanoma is lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, or uveal melanoma. In some embodiments, the active ingredient of the pharmaceutical composition consists of DCP. In some embodiments, the pharmaceutical composition further comprises at least one additional therapeutic agent or adjuvant therapy agent. In a specific embodiment, the additional therapeutic agent or adjuvant therapy agent may be selected from: folic acid, coenzyme Q10, curcumin, glutathione (GSH), aloe vera, oryzanol, 5-fluorouracil, and bortezomib. In some embodiments, the pharmaceutical composition comprises DCP and a pharmaceutically acceptable carrier or excipient.

In some embodiments, for prophylaxis or treatment of melanoma, the amount of DCP in the pharmaceutical composition administered to a subject may be about 0.005 to 20 mg/kg body weight, about 0.005 to 10 mg/kg body weight, about 0.005 to 5 mg/kg body weight, about 0.005 to 2.5 mg/kg body weight, 0.01 to 20 mg/kg body weight, about 0.01 to 10 mg/kg body weight, about 0.01 to 5 mg/kg body weight, about 0.01 to 2.5 mg/kg body weight, 0.1 to 20 mg/kg body weight, about 0.1 to 10 mg/kg body weight, about 0.1 to 5 mg/kg body weight, about 0.1 to 2.5 mg/kg body weight, 1 to 20 mg/kg body weight, about 1 to 10 mg/kg body weight, about 1 to 5 mg/kg body weight, or about 1 to 2.5 mg/kg body weight. In some embodiments, the amount of DCP is about 0.01 to 5 mg/kg body weight. In another embodiment, the amount of DCP is about 1 to 10 mg/kg body weight.

In some embodiments, the administration of the pharmaceutical composition comprising DCP may last at least 1, 2, 3, 4, 5, 6, 7, 8, 9, 10, 11, 12, 13, 14, 21, 28, 35, 42, 49, 56, 63, 70, 77, 84, 91 or 98 days. In some embodiments, the administering of the pharmaceutical composition comprising DCP may last at least one week. In some embodiments, the administering of the pharmaceutical composition comprising DCP may last at least two weeks. The preferred period of administration depends on the particular disease to be treated and the subject's specific conditions.

In some embodiments, for prophylaxis or treatment of melanoma, the pharmaceutical composition comprising the DCP is administered with i.v. injections or via the oral route. In some embodiments, for prophylaxis or treatment of melanoma, the pharmaceutical composition comprising the DCP is administered for at least one, two or three weeks.

The following examples are provided to describe and illustrate the present invention. As such, they should not be construed to limit the scope of the invention. Those in the art will well appreciate that many other embodiments also fall within the scope of the invention, as it is described hereinabove and in the claims.

Examples

The effects of DCP on leukemia, renal adenocarcinoma and melanoma can be demonstrated by results obtained from in vivo and in vitro studies and clinical trials. The scope of the invention, however, is not limited by the Examples herein provided.

Studies on Leukemia

Human promyelocytic leukemia cells (HL-60 cells) were cultured in vitro and cell viability was measured by quantifying cells numbers after treatment. The HL-60 cells were treated with a series of stepwise concentrations of DCP, carboplatin, etoposide and Methotrexate (MTX). After comparison of OD490 values of the tested agents and the control agents, an index of relative repression rate of cell proliferation was obtained. The $IC_{50}$ value was calculated by using the SPSS16.0 software. The $IC_{50}$ values of DCP, carboplatin, etoposide and MTX were 18.558 µM, 17.321 µM, 15.342 µM and 15.285 µM, respectively. The results are shown in FIG. 1.

Figure 2:
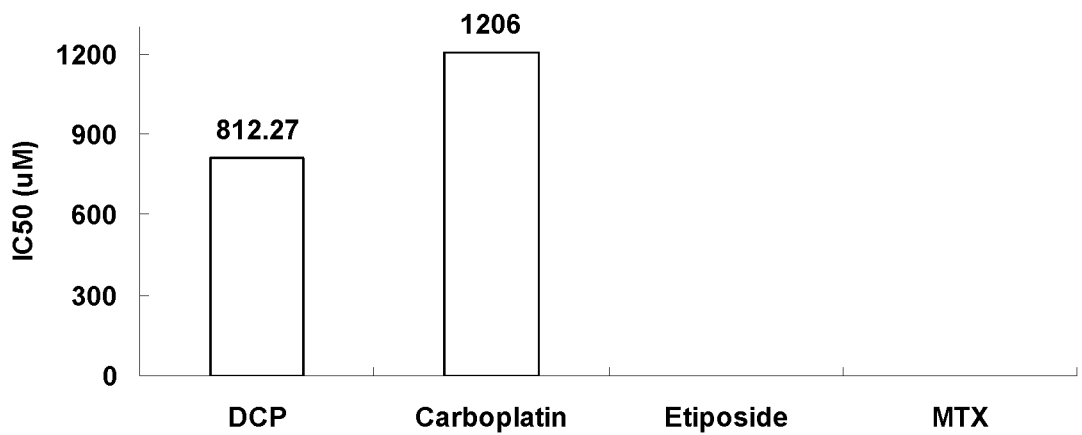
FIG. 2 shows the $IC_{50}$ values of tested and control agents in K562 cells, a cell line derived from a chronic myelogenous leukemia (CML) patient.

Human immortalized myelogenous leukemia cell line K562 cells were cultured in vitro and cell viability was measured by quantifying cells numbers after treatment. The K562 cells were treated with a series of stepwise concentrations of DCP, carboplatin, etoposide and MTX. After comparison of OD490 values of the tested agents and the control agents, an index of relative repression rate of cell proliferation was obtained. The $IC_{50}$ value was calculated by using the SPSS16.0 software. The $IC_{50}$ values of DCP and carboplatin were 812.27 µM and 1206 µM, respectively. Etoposide and MTX did not show any toxicity. The results are shown in FIG. 2.

Figure 3:
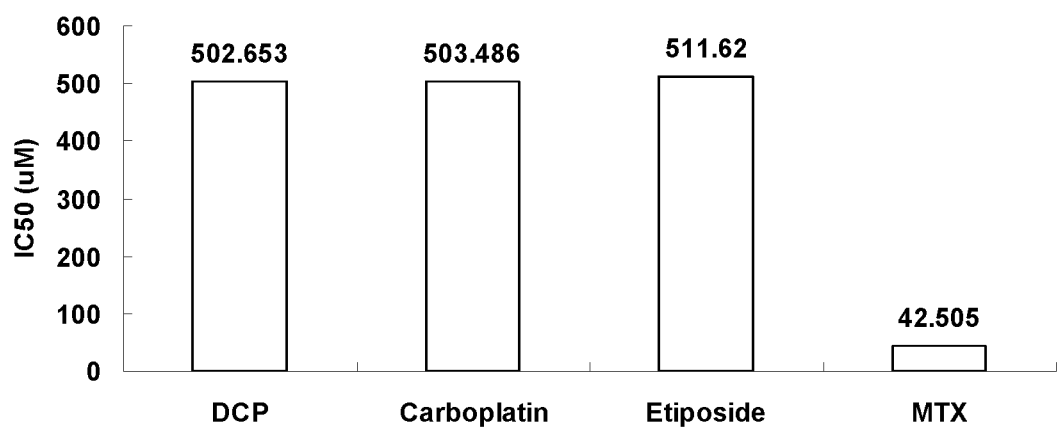
FIG. 3 shows the $IC_{50}$ values of tested and control agents in fetal hepatocytes HL-7002.

Human immortalized human fetal hepatic cell line HL-7002 cells were cultured in vitro and cell viability was measured by quantifying cells numbers after treatment. The HL-7002 cells were treated with a series of stepwise concentrations of DCP, carboplatin, etoposide and MTX. After comparison of OD490 values of the tested agents and the control agents, an index of relative repression rate of cell proliferation was obtained. The $IC_{50}$ value was calculated by using the SPSS16.0 software. The $IC_{50}$ values of DCP, carboplatin and etoposide were 502.653 µM, 503.486 µM and 511.62 µM, respectively. MTX showed little toxicity. The results are shown in FIG. 3.

Figure 4:
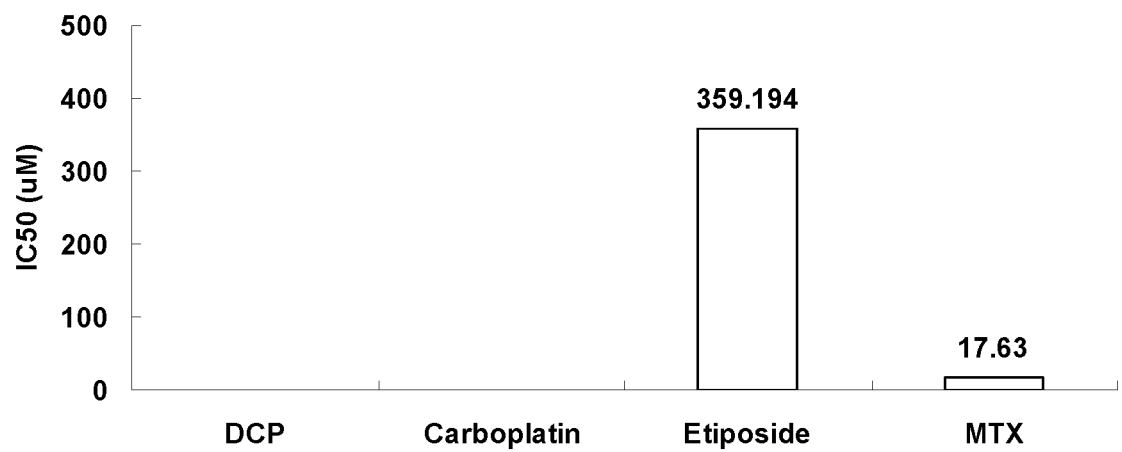
FIG. 4 shows the $IC_{50}$ values of tested and control agents in human embryonic kidney cell line HEK293.

Human embryonic kidney cell line HEK293 cells were cultured in vitro and cell viability was measured by quantifying cells numbers after treatment. The HEK293 cells were treated with a series of stepwise concentrations of DCP, carboplatin, etoposide and MTX. After comparison of OD490 values of the tested agents and the control agents, an index of relative repression rate of cell proliferation was obtained. The $IC_{50}$ value was calculated by using the SPSS16.0 software. The $IC_{50}$ values of etoposide and MTX were 359.194 µM and 17.63 µM, respectively. DCP and carboplatin showed no toxicity. The results are shown in FIG. 4.

In essence, the results demonstrate that the cellular toxicity of DCP is compatible to the control agents carboplatin, etiposide and MTX. K562, a chronical myelogenous leukemia (CML) cell line, was resistant to etiposide and MTX, but not DCP or carboplatin, but DCP showed a higher level of efficacy. In addition, while MTX showed significant cellular toxicity in normal hepatocyte HL-7002 cells, DCP, carboplatin and etiposide demonstrated very low level of toxicity. While DCP and carboplatin did not show any toxicity to HEK293 cells, etiposide demonstrated a low level of toxicity. Overall, DCP is effective in inducing leukemia cell death while preserving normal cells.

Cell culture: HL-60, K562, HL-7002 and HEK393 cells were purchased from ATCC. The cells were cultured in RPMI+5% Fetal Bovine Serum (FBS).

Drug treatment and cell viability (MTS) assay: The cells (105/100 mL/well) were cultured in a 96 well plate, and treated with DCP at step-wise concentrations from 0.01 uM to 300 uM. Cells treated with the solvents were used as negative controls, and carboplatin, etiposide and MTX were used as the positive controls. The cells were monitored daily, and the cell viability was evaluated with the Promega CellTiter 96 AQueous One Solution Cell Proliferation Assay (Promega, Madison, Wis., USA) according to the manufacture manuals. The cell viability was monitored at OD490 reading in a bio-spectrometer (Perkin Elmer, Walthan, Mass., USA).

Data analysis: The OD490 reading data were collected hourly from 1 h to 4 h after the addition of lysis buffer. The index of cell growth repression ratio was obtained by comparing the OD490 data of treatment to the negative control. The drug response rate IC50 was calculated with the SPSS 16.0 software.

Figure 5:
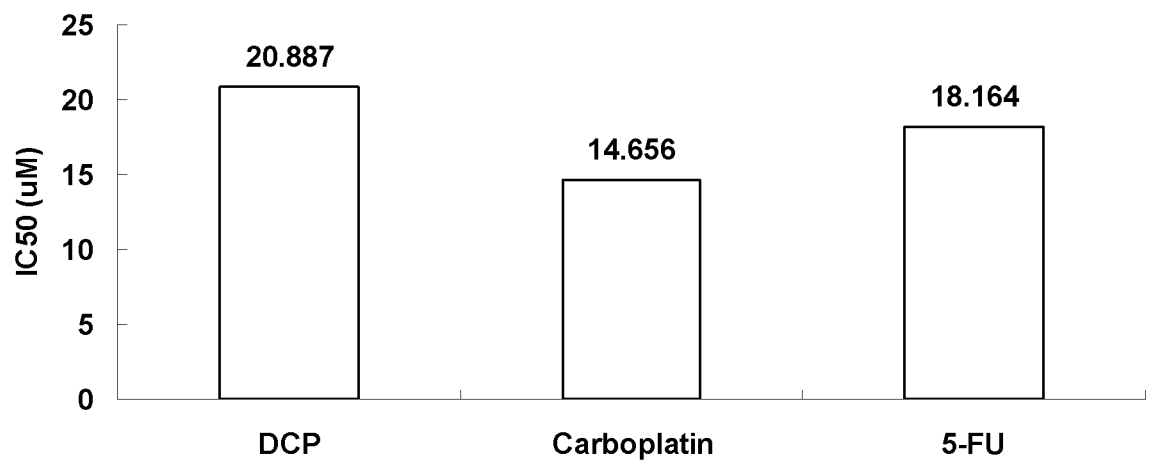
FIG. 5 shows the $IC_{50}$ values of tested and control agents in A498 cells, a renal carcinoma cell line.

Studies on renal adenocarcinoma cells Renal carcinoma cell line A498 cells were cultured in vitro and cell viability was measured by quantifying cells numbers after treatment. The A498 cells were treated with a series of stepwise concentrations of DCP, carboplatin and fluorouracil (5-FU). After comparison of OD490 values of the tested agents and the control agents, an index of relative repression rate of cell proliferation was obtained. The $IC_{50}$ value was calculated by using the SPSS16.0 software. The $IC_{50}$ values of DCP, carboplatin, etoposide and 5-FU were 20.887 µM, 18.357 µM and 18.164 µM, respectively. The results are shown in FIG. 5.

Figure 6:
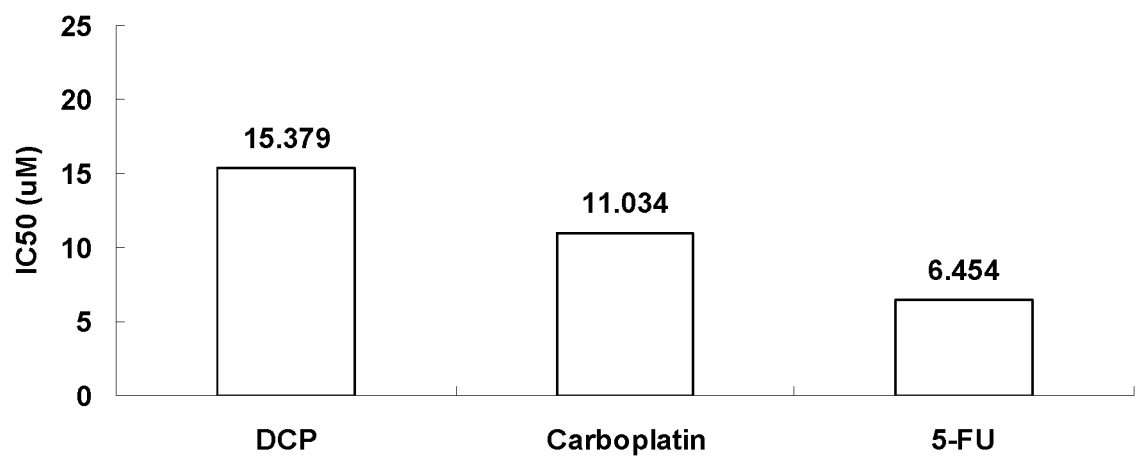
FIG. 6 shows the $IC_{50}$ values of tested and control agents in ACHN cells, a renal carcinoma cell line.

Renal carcinoma cell line ACHN cells were cultured in vitro and cell viability was measured by quantifying cells numbers after treatment. The ACHN cells were treated with a series of stepwise concentrations of DCP, carboplatin and fluorouracil (5-FU). After comparison of OD490 values of the tested agents and the control agents, an index of relative repression rate of cell proliferation was obtained. The $IC_{50}$ value was calculated by using the SPSS 16.0 software. The $IC_{50}$ values of DCP, carboplatin and 5-FU were 15.379 µM, 11.034 µM and 6.454 µM, respectively. The results are shown in FIG. 6.

Figure 7:
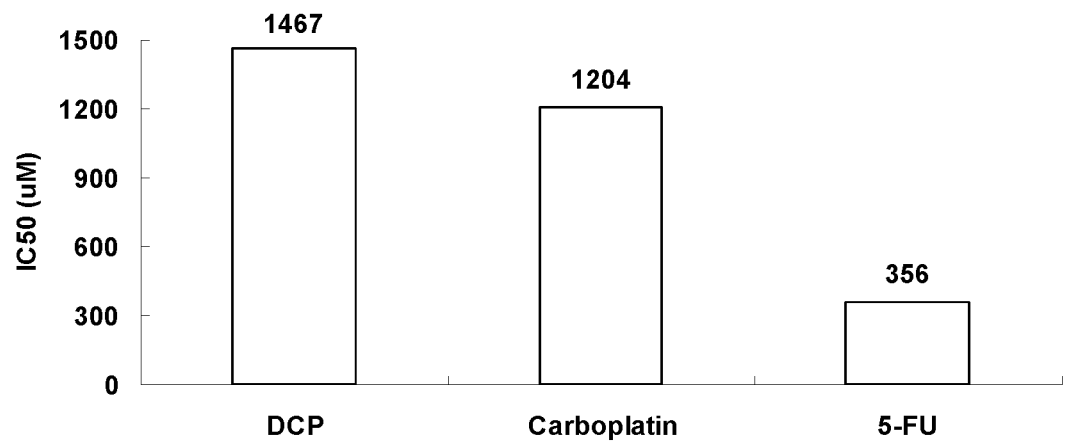
FIG. 7 shows the $IC_{50}$ values of tested and control agents in HL-7002 cells, a cell line of normal hepatocytes.

HL-7002 cells were cultured in vitro and cell viability was measured by quantifying cells numbers after being treated with a series of stepwise concentrations of DCP, carboplatin and 5-FU. After comparison of OD490 values of the tested agents and the control agents, an index of relative repression rate of cell proliferation was obtained. The $IC_{50}$ value was calculated by using the SPSS16.0 software. The $IC_{50}$ values of DCP, carboplatin and 5-FU were 1467 µM, 1410.23 µM and 356 µM, respectively. The results are shown in FIG. 7.

Figure 8:
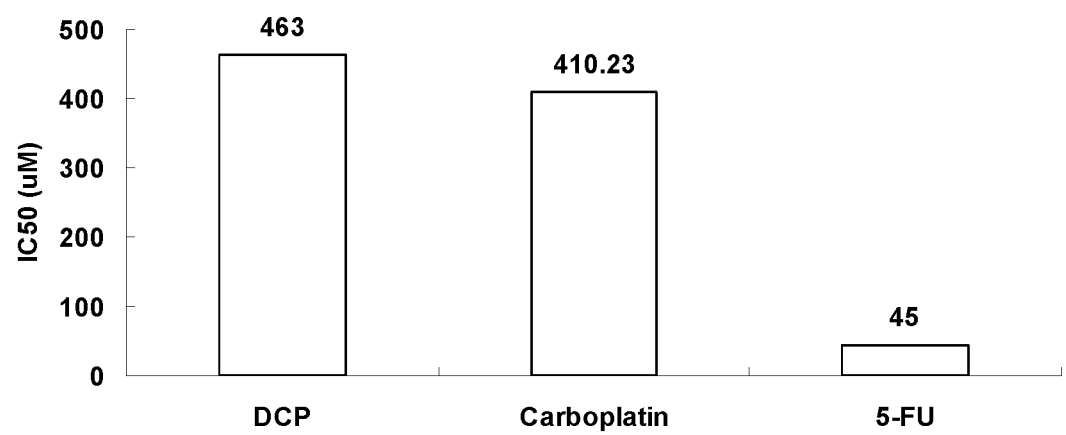
FIG. 8 shows the $IC_{50}$ values of tested and control agents in HEK293, a cell line of normal embryonic kidney cells.

HEK293 cells were cultured in vitro and cell viability was measured by quantifying cells numbers after being treated with a series of stepwise concentrations of DCP, carboplatin and 5-FU. After comparison of OD490 values of the tested agents and the control agents, an index of relative repression rate of cell proliferation was obtained. The $IC_{50}$ value was calculated by using the SPSS16.0 software. The $IC_{50}$ values of DCP, carboplatin and 5-FU were 463 µM, 410.23 µM and 45 µM, respectively. The results are shown in FIG. 8.

In essence, the results demonstrated that the cellular toxicity of DCP in A498 and ACHN cells was slightly weaker than carboplatin and 5-FU. In addition, the experiments also showed that the cellular toxicity of DCP in HL-7002 cells, which are normal hepatocytes, and in HEK293 cells, which are normal embryonic kidney cells, was weaker compared to carboplatin and much weaker than 5-FU (4-fold lower).

DCP is used in treatment of renal adenocarcinoma in comparison to carboplatin and 5-FU, which are widely accepted as effective medications renal adenocarcinoma patients. Though the effects of DCP are slightly weaker than carboplatin and 5-FU in suppressing cell viability of renal adenocarcinoma cells, DCP shows weaker toxicity in normal cells, indicating less severe side effects for the cancer patients. Overall, DCP is effective in inducing renal adenocarcinoma cell death while preserving normal cells.

Cell culture: A498 and ACHN cells were purchased from Tongbai Bio (Shanghai, China). HL-7002 and HEK393 cells were purchased from ATCC. The cells were cultured in RPMI+5% Fetal Bovine Serum (FBS).

Drug treatment and cell viability (MTS) assay: The cells (105/100 mL/well) were cultured in a 96 well plate, and treated with DCP at step-wise concentrations from 0.01 uM to 300 uM. Cells treated with the solvents were used as negative controls, and carboplatin, and 5-FU were used as the positive controls. The cells were monitored daily, and the cell viability was evaluated with the Promega CellTiter 96 AQueous One Solution Cell Proliferation Assay (Promega, Madison, Wis., USA) according to the manufacture manuals. The cell viability was monitored at OD490 reading in a bio-spectrometer (Perkin Elmer, Walthan, Mass., USA).

Data analysis: The OD490 reading data were collected hourly from 1 h to 4 h after the addition of lysis buffer. The index of cell growth repression ratio was obtained by comparing the OD490 data of treatment to the negative control. The drug response rate $IC_{50}$ was calculated with the SPSS 16.0 software.

Studies on Melanoma Patients

The following case summarizes DCP's pharmaceutical use on a melanoma patient with multiple metastases in the brain and adrenal grand. A metastatic tumor mass firstly was detected at the right frontal and parietal lobe of a patient's brain by MRI, and was removed by surgery in one month later. However, a new tumor mass with edema around it was detected at the left of parietal lobe. The tumor grew bigger, and the edema around the tumor became worse about two months after the new tumor was detected. The patient was treated with DCP solution (150 mg of DCP in 250 mL aqueous solution one time for every three days) for about three weeks. MRI showed the tumor shrunk, and the edema around the tumor was relieved.

Figure 9:
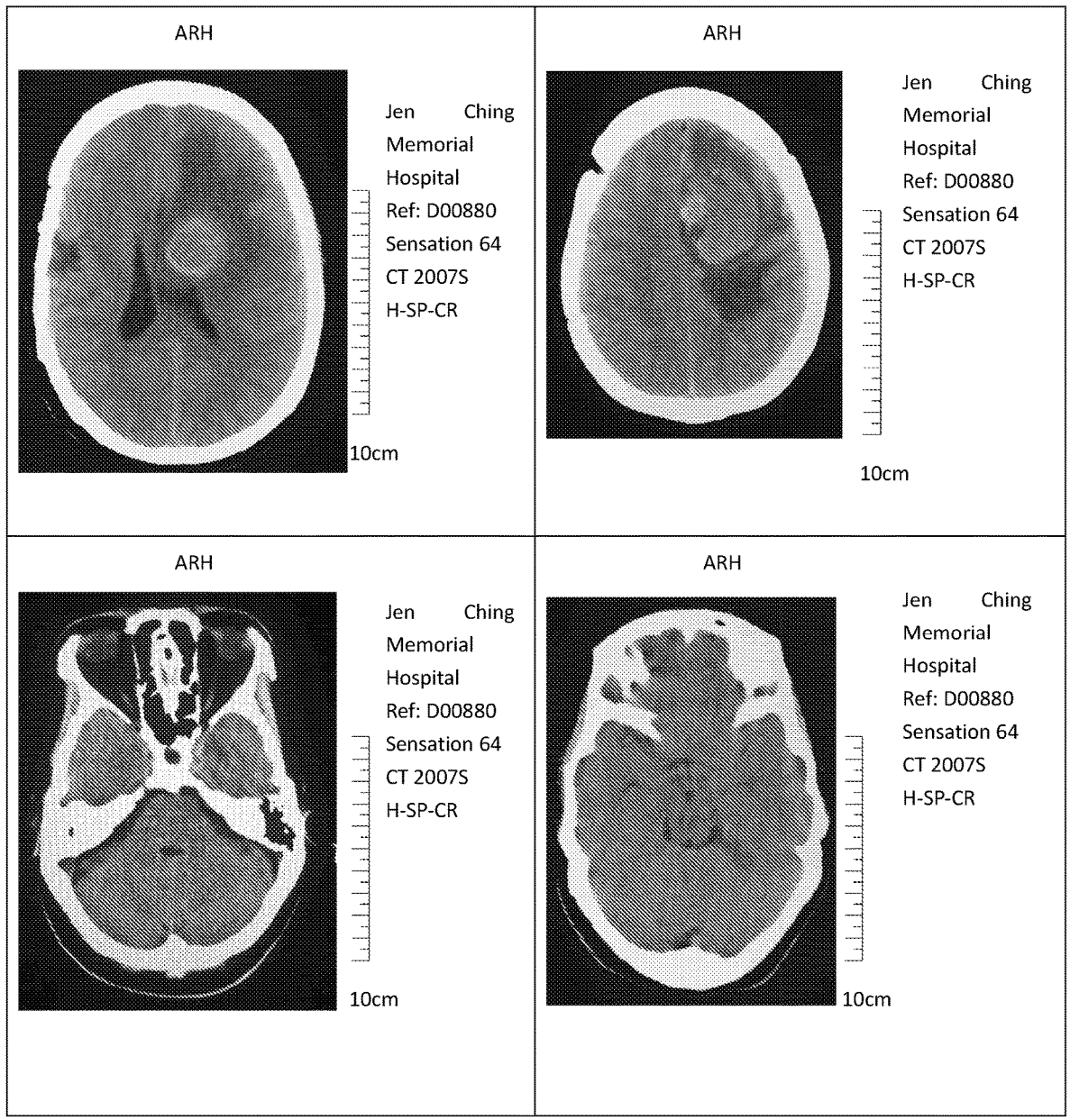
FIG. 9 shows computed tomography (CT) pre-chemo of a melanoma patient with multiple metastases in the brain and adrenal grand.

Pre-chemo CT indicated that the tumor mass was fairly large at the left of parietal lobe of brain, with edema around the tumor (FIG. 9). The left lateral ventricle was compressed. The sign of removed tumors could be distinguished at the right frontal and parietal lobe, and the postoperative repair was found in the right frontal parietal bone. The midline structure shifted to the right side.

Figure 10:
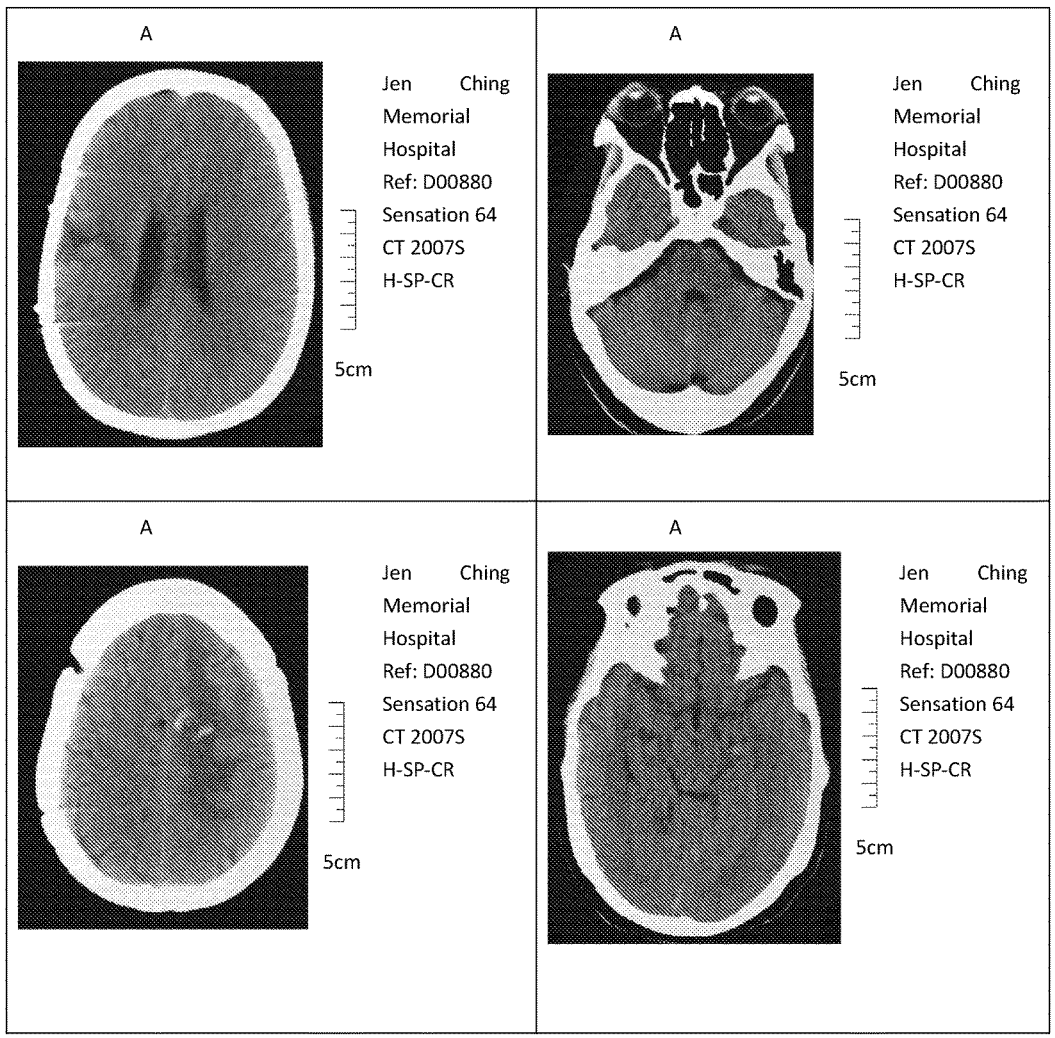
FIG. 10 shows CT post-chemo of a melanoma patient with multiple metastases in the brain and adrenal grand.

After treatment with DCP solution for about three weeks, the patient was examined (FIG. 10). The post-chemo CT indicated that the tumor mass at the left of parietal lobe shrunk comparing with the pre-chemo CT, and the edema around the tumor has been significantly relieved. The tumors at the right frontal and parietal lobe were removed, and the midline structure was normal.

Sample Pharmaceutical Composition Comprising DCP and Administration

Aqueous or solid pharmaceutical composition of the present invention comprises an effective amount of DCP, with or without an appropriate amount of at least one additional therapeutic agent or adjuvant. DCP, as well as the therapeutic agent or adjuvant, may be dissolved or dispersed in a pharmaceutical acceptable carrier or aqueous media.

Depending on the particular cancer to be treated, administration of pharmaceutical composition according to the present invention can via any common route as long as the target issue is available via the route. For example, the pharmaceutical composition may be administered by infusion, injection, or via the oral route.

A number of pharmaceutical compositions were produced:

Pharmaceutical composition sample A: 70 g of DCP was dissolved in pre-treated normal saline or 5% of aqueous glucose (in water) and the final volume of the solution was adjusted to 5.0 L. Then the solution was filtered through 0.22 um filter and dispersed into ample bottles with 50.0 mL in each.

What is claimed is:

1. A method of treating a disease in a subject, comprising administering a pharmaceutical composition comprising dicycloplatin (DCP) to the subject,
    wherein the disease is melanoma with brain metastasis, or brain edema associated with metastatic melanoma,
    and wherein
        a) the pharmaceutical composition consists of DCP as the only active ingredient and a pharmaceutically acceptable carrier or excipient; or
        b) the pharmaceutical composition consists of DCP and at least one agent selected from the group consisting of folic acid, coenzyme Q10, curcumin, glutathione (GSH), aloe vera, oryzanol, 5-fluorouracil, and bortezomib, and a pharmaceutically acceptable carrier or excipient.

2. The method of claim 1, wherein the disease is melanoma with brain metastasis.

3. The method of claim 1, wherein the pharmaceutical composition is administered to the subject orally or via an injection.

4. The method of claim 1, wherein the amount of DCP in the pharmaceutical composition administered to the subject is at an amount of about 0.01 to 10 mg/kg body weight.

5. The method of claim 1, wherein the pharmaceutical composition the pharmaceutical composition consists of DCP as the only active ingredient and a pharmaceutically acceptable carrier or excipient.

6. The method of claim 5, wherein the pharmaceutical composition is administered to the subject via an injection.

7. The method of claim 5, wherein the pharmaceutical composition is administered to the subject orally.

8. The method of claim 5, wherein the amount of DCP in the pharmaceutical composition administered to the subject is at an amount of about 0.01 to 10 mg/kg body weight.

9. The method of claim 6, wherein the amount of DCP in the pharmaceutical composition administered to the subject is at an amount of about 0.01 to 10 mg/kg body weight.

10. The method of claim 7, wherein the amount of DCP in the pharmaceutical composition administered to the subject is at an amount of about 0.01 to 10 mg/kg body weight.

11. The method of claim 1, wherein the disease is brain edema associated with metastatic melanoma.

* * * * *